United States Patent [19]

DeFonce

[11] Patent Number: 5,009,223
[45] Date of Patent: Apr. 23, 1991

[54] VARIABLE AXIS KNEE BRACE
[76] Inventor: Michael A. DeFonce, 12149 Mirror Lake, Creve Coeur, Mo. 63146
[21] Appl. No.: 415,623
[22] Filed: Oct. 2, 1989
[51] Int. Cl.$^5$ ............................................. A61F 5/00
[52] U.S. Cl. .................................. 128/80 C; 128/80 R; 623/39
[58] Field of Search ................. 128/80 R, 80 C, 80 F, 128/80 E, 80 H, 77; 623/39

[56] References Cited
U.S. PATENT DOCUMENTS

| 3,779,654 | 12/1973 | Horne . | |
|---|---|---|---|
| 4,041,940 | 8/1977 | Frankel et al. | 128/80 C |
| 4,463,751 | 8/1984 | Bledsoe . | |
| 4,633,867 | 1/1987 | Kausek et al. . | |
| 4,655,201 | 4/1987 | Pirmantgen . | |
| 4,699,129 | 10/1987 | Aaserude et al. . | |
| 4,723,539 | 2/1988 | Townsend . | |
| 4,854,308 | 8/1989 | Drillio | 128/80 C |

FOREIGN PATENT DOCUMENTS 2600528 12/1987 France ............................. 128/80 C Primary Examiner—Richard J. Apley
Assistant Examiner—Lynne A. Reichard
Attorney, Agent, or Firm—Haverstock, Garrett & Roberts

[57] ABSTRACT

This invention comprises a knee brace for controlling knee instability and minimizing risk of injury to the knee in all types of sports. The mechanical hinge has the same kinematics as the human knee, allowing the knee brace to conform to the upper and lower leg throughout its range of motion. The knee brace includes a femoral brace and a tibial brace joined by unique variable axis hinges wherein arcuate slots are formed in each link with respective followers disposed on opposing links to provide rotation and slide movement between the femur and tibia resulting in the same path of the center rotation as the human knee. The femoral brace is conformed to the upper leg to provide maximum stability and protection. The tibial brace is conformed to the tibia tubercle, just below the patella and frontal area of the tibia, to provide maximum stability and protection therefor.

13 Claims, 9 Drawing Sheets

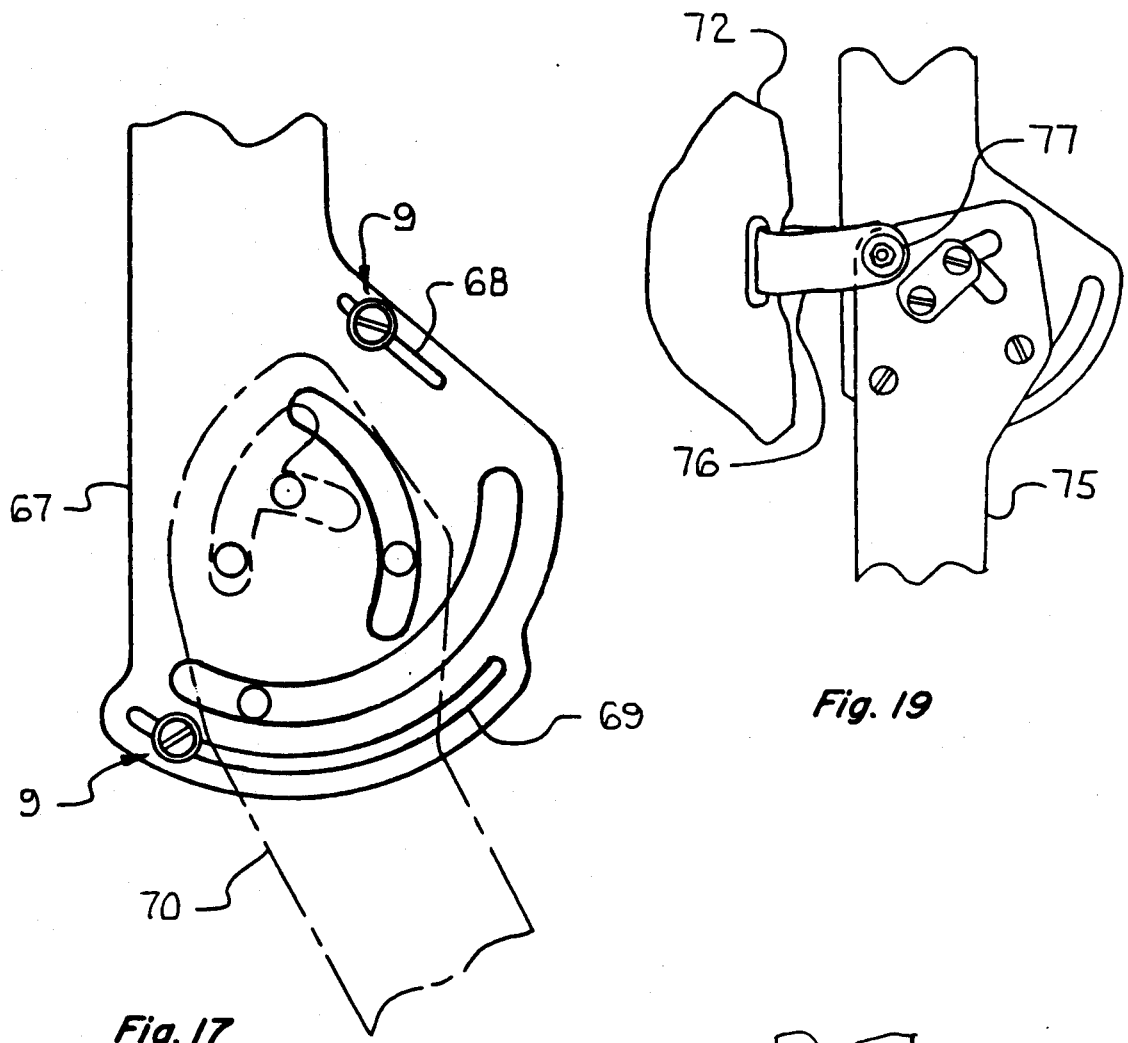
Fig. 17
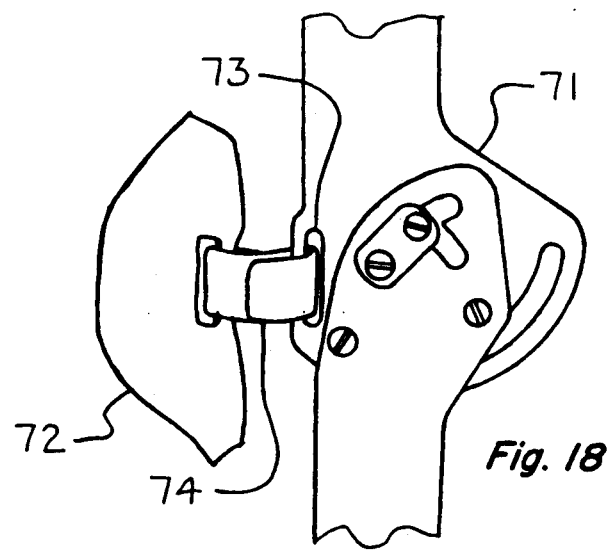
Fig. 19
Fig. 18

VARIABLE AXIS KNEE BRACE

BACKGROUND OF THE INVENTION

This invention comprises a knee brace for stabilization and protection of a human knee joint with its hinge designed to have the same kinematics as the human knee. This brace is specially designed for most athletic sports, particularly contact sports, which involve potential knee injuries. It may be worn by athletes who have severely weakened knee joints so that the athletes may participate in their sport without fear of reinjuring the knee.

The typical knee brace used in sports medicine consists of a single pivot pin or double pivot pins known as polycentric hinges. These types of hinges prevent leg braces from conforming to the wearer's leg through all range of motion of the knee. Among such braces are the HT Racing Brace by HT Racing of Placentia, Calif., Ortho-Tech Brace by The One Shop of Westwood, Calif., Lennox Hill Derotation Brace by Lennox Hill Brace of Long Island City, NY, C.T.I. Brace by Innovation Sports of Irvine, Calif., AMX 2 EVS Brace by Fairing Imports of Beverly Hills, Calif., and Pro-Am Brace by Pro-Am Braces, Inc, of Boston, Ma..

The following patents are attempts in achieving the same kinematics as the human knee.

U.S. Pat. No. 4,723,539 of Townsend discloses a knee joint hinge with two curved slots and a straight slot segmented to each curved slot on the femoral member, and with two pins on the tibial member. This hinge rotates and slides for a predetermined articulation then rotates about the center.

U.S. Pat. No. 4,655,201 of Pirmantgen discloses a knee joint hinge with a narrow arcuate bearing surface of varying radii of curvature on the femoral member, and a horizontal elongated slot on the tibial side bar.

U.S. Pat. No. 4,699,129 of Aaserude is essentially a polycentric hinge.

U.S. Pat. No. 4,463,751 of Bledsoe discloses a knee joint hinge with two arcuate cam slots on the femoral members, two pins on the tibial members and also including circular toothed plates with slots for restricting the range of articulation.

SUMMARY OF THE INVENTION

The present invention includes a femoral brace and tibial brace on the leg and means for connecting the femoral brace and tibial brace in hinged relationship. The femoral brace and tibial brace are custom made for each individual via plaster casting or other means. The main member of the femoral brace runs parallel along the middle of the upper leg and is joined to a member that conforms to the upper leg above the knee and also joined perpendicularly to a curved member partially up the upper leg. The main member of the tibial brace runs parallel along the tibia and is joined by a member that conforms to the frontal portion of the tibia just beneath the patella. The straight member is also joined perpendicularly to a curved member partially down the lower leg depending on the size of the calf muscles.

The present invention also includes a unique variable axis hinge which is designed with a novel "four-bar linkage." The femoral joint element has two femoral arcuate slots; namely, a femoral anterior arcuate slot and a femoral posterior arcuate slot, and two femoral followers which are located at the centers of curvature of the femoral arcuate slots. The tibial joint element has two tibial slots in a T form; namely, a tibial anterior arcuate slot and a tibial posterior arcuate joined slot at a T angle, and two tibial followers which are located at the centers of curvature of the tibial arcuate slots. Each follower engages an arcuate slot on the joint element opposite to the one on which it is located. At the joint, the femoral and tibial elements rotate and slide with respect to each other forming a path of the center of rotation similar to the rotation of the human knee. To prevent lateral displacement of the femur with respect to the tibia, condylar pads are placed on the medial and lateral sides of the hinged joint which engage the medial and lateral sides of the knee. It will be apparent that, modifications can be made to the variable axis hinge to achieve the same results and such changes are not excluded from the content of this disclosure.

DESCRIPTION OF THE DRAWINGS

FIGS. 16 and 17 are side views of the mechanical hinge modified to permit limitations of flexion and extension of the human knee;

FIG. 18 is a side view of the mechanical hinge modified to permit mounting a knee cup onto the femoral link;

FIG. 19 is a side view of the mechanical hinge modified to permit mounting a knee cup onto the tibial link;

DETAILED DESCRIPTION OF THE INVENTION

Figure 1:
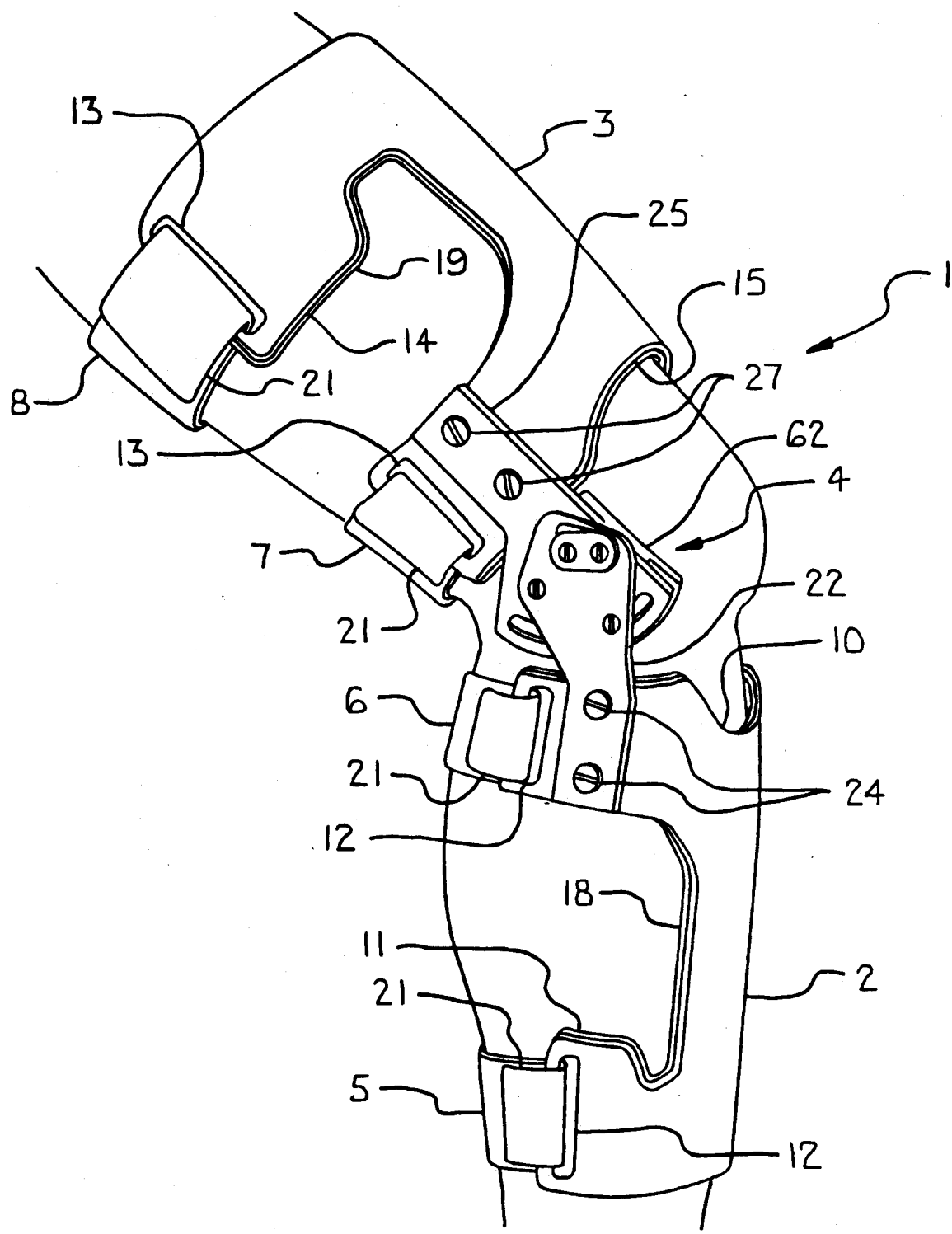
FIG. 1 ia a perspective view of the right knee brace of this invention viewed from the outer side of the flexed right leg.
Figure 2:
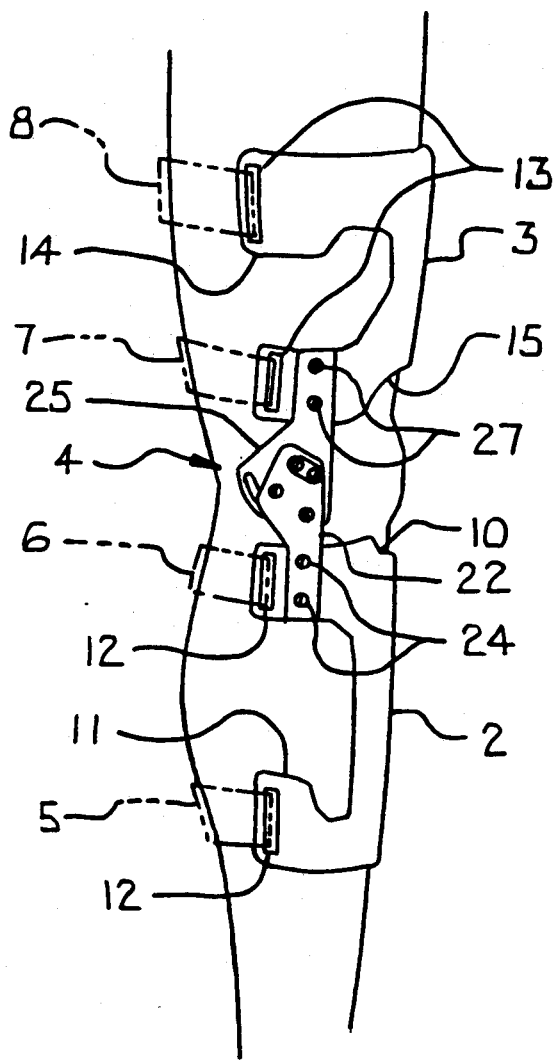
FIG. 2 is a perspective view of the right knee brace viewed from the right side with straps shown in dotted outline for clarity.
Figure 3:
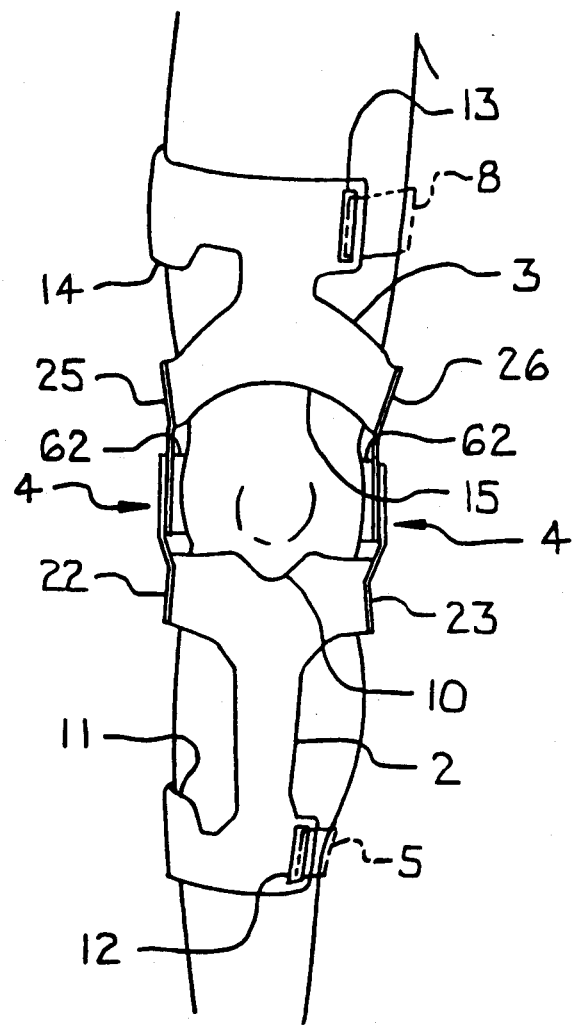
FIG. 3 is a perspective view of the right knee brace viewed from the front.
Figure 4:
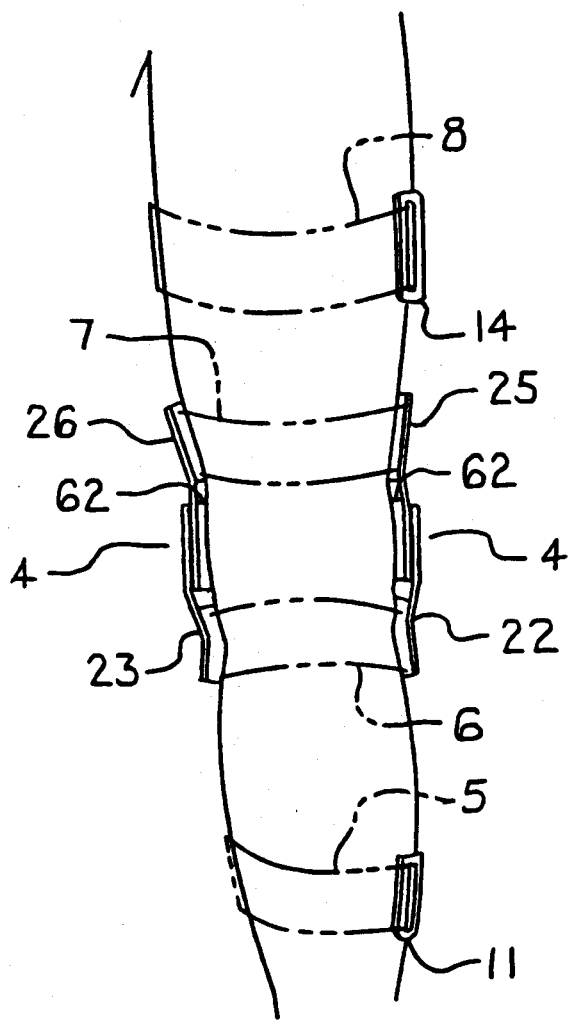
FIG. 4 is a perspective view of the right knee brace viewed from the rear.
Figure 5:
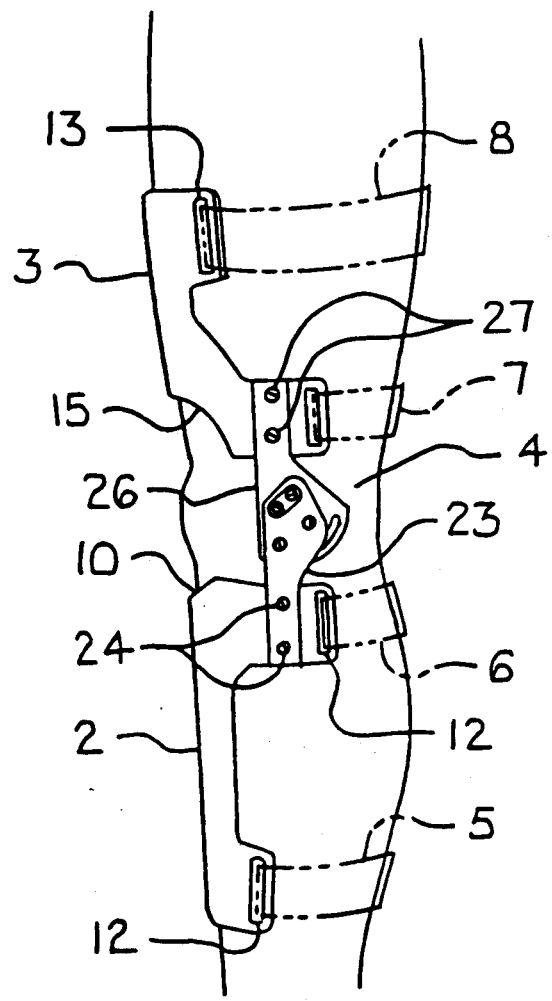
FIG. 5 is a perspective view of the right knee brace viewed from the left side.

The knee brace 1 of this invention shown in FIG. 1 includes a tibial brace 2, a femoral brace 3, a variable axis mechanical hinge 4 which joins the tibial brace and femoral brace, a pair of tibial straps 5 and 6, a pair of femoral straps 7 and 8, and a condylar pad 62. The knee brace shown is made for the right leg; however, a mirror image of the knee brace can be used on the left leg.

For precise fit, the tibial and femoral braces are custom made to fit the same leg which is to wear the knee brace. This requires a thin cast formed over a wearer's leg. The cast is then cut and removed, and thereupon serves as a model of the wearer's leg. Thin sheets of aircraft grade aluminum are cut and formed over the cast. Once the sheet metal pieces (one for the femoral brace and another for the tibial brace) have been cut and formed, they are ready to be used as an internal mold which will become a permanent piece of the brace. A combination of graphite, Kevlar and S-glass composites can be used in a light resin which are then formed over the internal mold to create the femoral and tibial braces.

Figure 6:
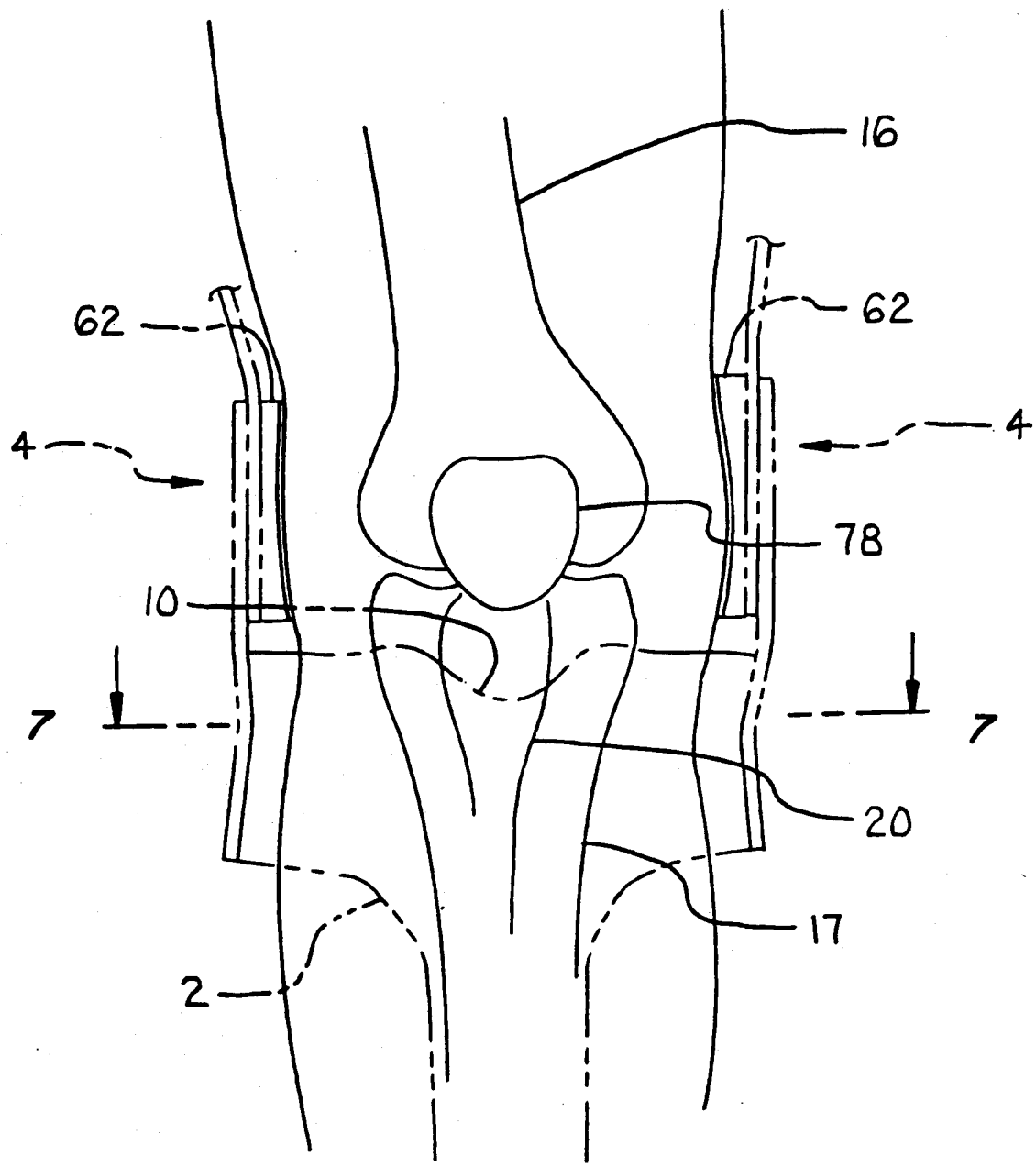
FIG. 6 is a front view of the right knee and parts of the knee brace of the present invention which parts are shown in dotted outline.
Figure 7:
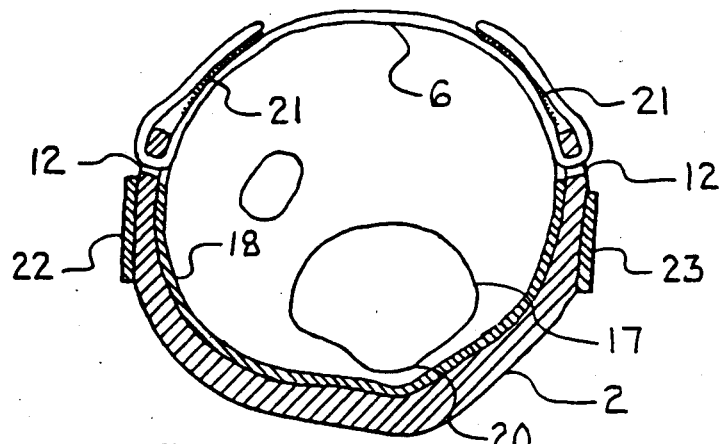
FIG. 7 is a sectional view of the lower leg and tibial brace taken along line 7—7 of FIG. 6.

The tibial brace 2, shown in FIGS. 1, 2, 3, 4 and 5, is shaped to fit over the frontal portion of the lower leg. The top portion of this brace partially encircles the leg and conforms to the tibia tubercle 20, as shown in FIGS. 6 and 7. This minimizes the displacement of the tibia 17 with respect to the femur 16 of the weakened knee. A concave or V-shaped notch 10 on the top portion of the tibial brace 2 adds comfort to the wearer by minimizing pressure on the patella tendon and the lower portion of the patella 78 when the lower leg is in extension. The lower portion of the tibial brace 2, joined by a connecting portion lying along the front of the lower leg, partially encircles the frontal and lateral portion of the lower leg just beneath the calf muscles. A paddle or end of such lower portion 11 is enlarged to prevent the tibial brace 2 from sinking into the soft tissue. The entire inner surface of the tibial brace may be lined with shock absorbing materials 18, such as polyurethane or polyethylene foam, for comfort. The unique features of the tibial brace are the integral slots 12, which eliminate the need for separate D-rings, straps and extra fasteners. Two large straps 5 and 6 with Velcro closure 21 secure the tibial brace to the lower leg.

The femoral brace 3 shown in FIGS. 1, 2, 3, 4 and 5 is shaped to fit over the frontal upper leg. The connecting member of the femoral brace 3 runs along parallel to the middle of the front of the upper leg. The lower portion of the femoral brace partially encircles the upper leg just above the knee. The lower edge 15 of the femoral brace is formed as an elongated semicircle which minimizes pressure on the quadriceps muscles. The upper portion of the femoral brace 3 partially encircles the frontal and lateral portion of the upper leg at approximately halfway up the thigh. The "paddle" 14 is enlarged to prevent the femoral brace from sinking into the soft tissue. The entire inner surface of the femoral brace may be lined with shock absorbing material 19, such as polyurethane or polyethylene foam, for comfort. The unique features of the femoral brace are the intergral slots 13 which eliminate the need for separate D-rings, straps, and extra fasteners. Two large straps 7 and 8 with Velcro closures 21 secure the femoral brace to the upper leg.

The main feature of this invention lies in the mechanical design of the hinge 4 which joins the tibial brace 2 and femoral brace 3; all of which, when combined to form the knee brace, is capable of stabilizing the wearer's leg through all phases of articulation. It will be appreciated that the lateral hinge is the mirror image of the medial hinge, and that both will operate in synchronization as the leg is flexed. The mechanical hinge and its various parts are preferably formed of metal for desired strength.

The tibial brace 2 is provided with spaced parallel links 22 and 23 as shown in FIGS. 1, 2, 3, 4 and 5. Link 22 is the lateral link and link 23 is the medial link. The links 22 and 23 are fixed by fastener means 24 onto the tibial brace; however, the links 22 and 23 may be integrated into the tibial brace, without departure from the invention. The free end of each link 22 and 23 terminates in a widened end.

The femoral brace 3 is provided with spaced parallel links 25 and 26; link 25 is the lateral link and link 26 is the medial link. The links 25 and 26 are fixed by fastener means 27 onto the femoral brace. Alternatively, they may be integrated into the femoral brace without departure from the invention. The free end of each link 25 and 26 terminates in a widened end.

Figures 8, 9:
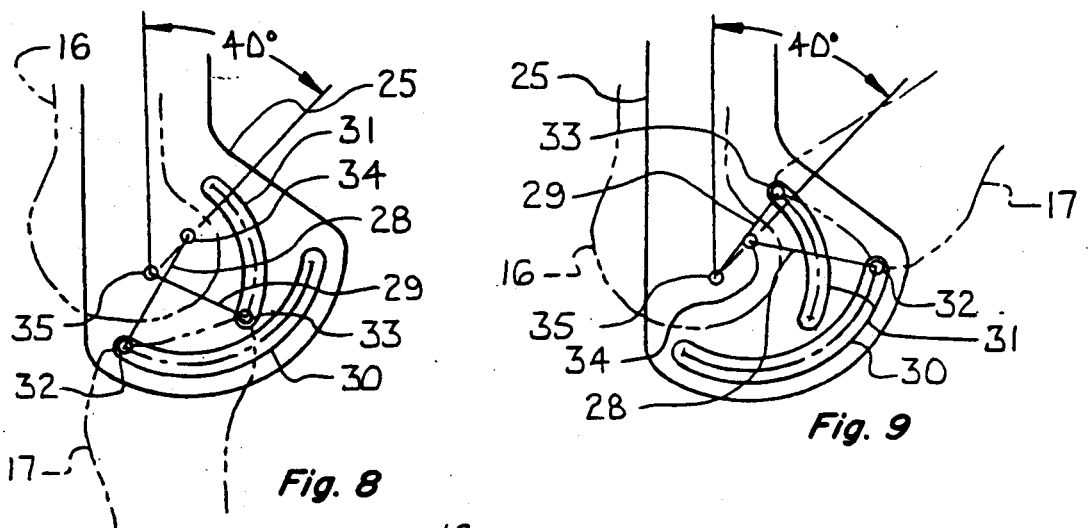
FIGS. 8 and 9 are side views of a femoral link superimposed on the human knee joint, the bones thereof partially shown in dotted outline.

The unique mechanical hinge employs a novel "four-bar linkage." FIGS. 8 and 9 show the femoral link 25 superimposed over the human knee, including a femur 16, tibia 17, anterior cruciate ligament 28, and posterior cruciate ligament 29. FIG. 8 shows the tibia at full extension and FIG. 9 shows the tibia at full flexion. For the sake of simplicity, other details of the knee joint are not shown. The femoral anterior arcuate slot 30 and femoral posterior arcuate slot 31 represent the path of the tibial end attachment points 32 and 33 of the anterior cruciate ligament 28 and posterior cruciate ligament 29, respectively, with the femur 16 fixed and the tibia 17 allowed to move. The respective femoral end attachment points 34 and 35 of the cruciate ligaments 28 and 29 form the centers of the curvature of the femoral arcuate slots 30 and 31, respectively. To allow normal mobility of the knee joint, the femoral attachment end points 34 and 35 must preferably lie on a line which forms an approximately 40° angle (as shown if FIGS. 8 and 9) with long axis of the femur 16.

Figures 10, 11:
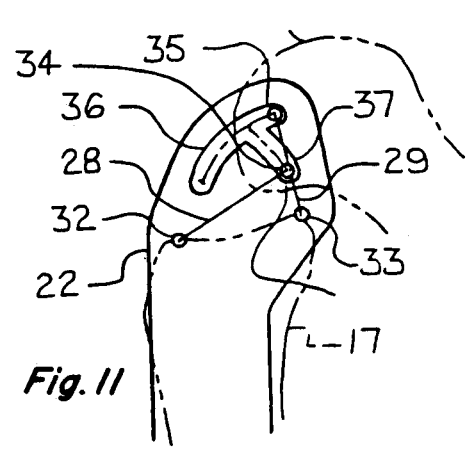
FIGS. 10 and 11 are side views of a tibial link superimposed on the human knee joint the bones thereof partially shown in dotted outline.

The tibial link 22, as shown in FIGS. 10 and 11, is superimposed over the human knee similarly to the femoral link 25 shown in FIGS. 8 and 9 except that the femur 16 is shown at full extension and flexion, respectively, and the tibia 17 is fixed. The combined intersecting tibial anterior arcuate slot 37 and tibial posterior arcuate slot 36 represent the paths of the femoral end attachment points 34 and 35 of the anterior cuciate ligament 28 and posterior cruciate ligament 29, respectively, with the tibia 17 fixed and the femur 16 allowed to move. The tibial end attachment points 32 and 33 of the cruciate ligaments 28 and 29 form the centers of curvature of the tibial arcuate slots 37 and 36, respectively.

Figures 12, 13:
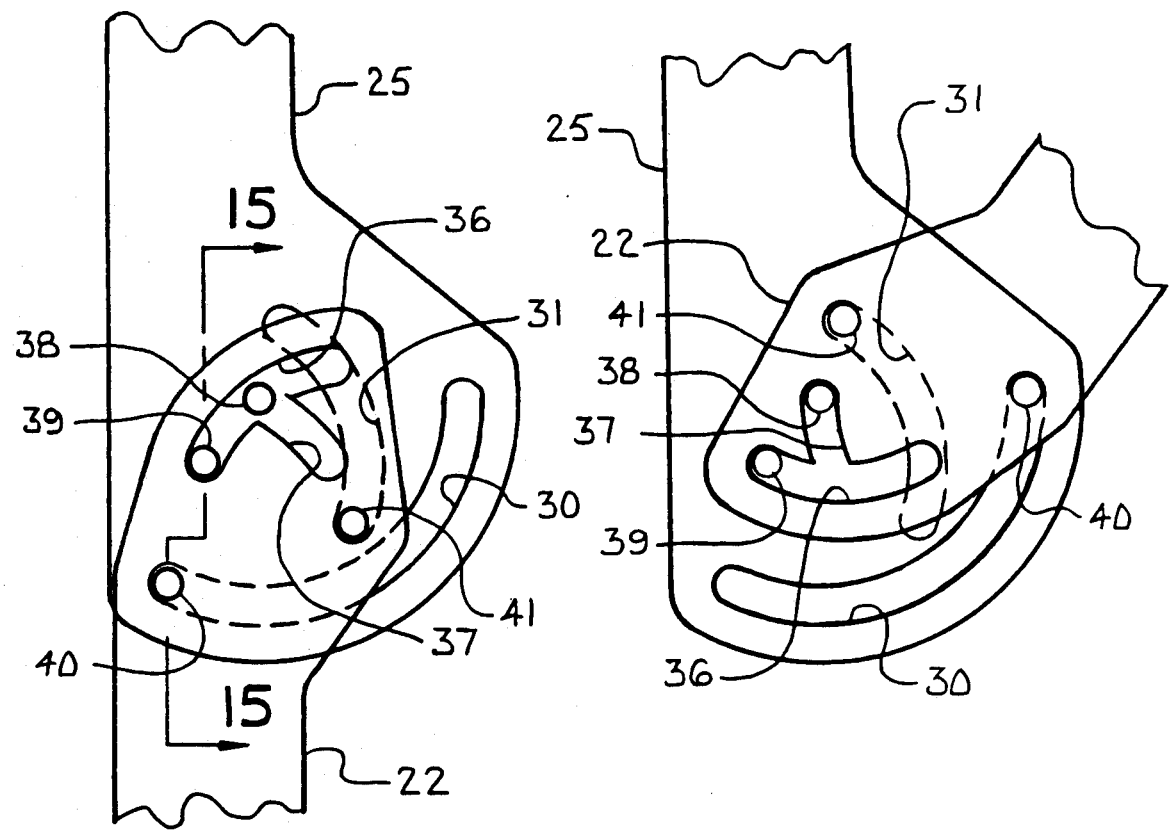
FIGS. 12 and 13 are side views of a mechanical hinge of the present invention.

FIGS. 12 and 13 show the completed hinge with the tibial link 22 overlapping the femoral link 25. The femoral followers 38 and 39 are located at the femoral end attachment points 34 and 35 (see FIGS. 8 and 9) of the cruciate ligaments. The femoral followers 38 and 39 move in the intersecting tibial anterior arcuate slot 37 and tibial posterior arcuate slot 36, respectively. In like manner, the tibial followers 40 and 41 are located at the tibial end attachment points 32 and 33 (see FIGS. 8 and 9) of cruciate ligaments. The tibial followers 40 and 41 move in the femoral anterior arcuate slot 30 and femoral posterior arcuate slot 31, respectively. The overlapping femoral link and tibial link can be best seen in FIG. 15 which is a sectional view of the hinge of FIG. 12.

It should be noted that using the combination of any two or three of the previously defined slots with corresponding followers for each such slot, with the exception of a combination of the tibial anterior slot 37 and tibial posterior slot 36 only, will result in the same motion by the knee as results from the use of a hinge with all four of the slots with corresponding followers as described above. In other words the same motion will be described by the knee joint when the hinge employs both the femoral anterior and posterior slots together with a single tibial slot either anterior and posterior, when it employs a single femoral slot either anterior and posterior with both the tibial anterior and posterior slots, when it employs a single femoral slot together with a single tibial slot and when it uses only the two femoral anterior and posterior slots with no tibial slots, where in every case corresponding followers in bearing engagement with such slots are present on the respective complementary link. The four slot hinge is preferred over the two or three slot hinge because the four slot hinge offers more stability to a joint when subjected to a blow on its side normal to the lateral or medial plates or links.

Figure 14:
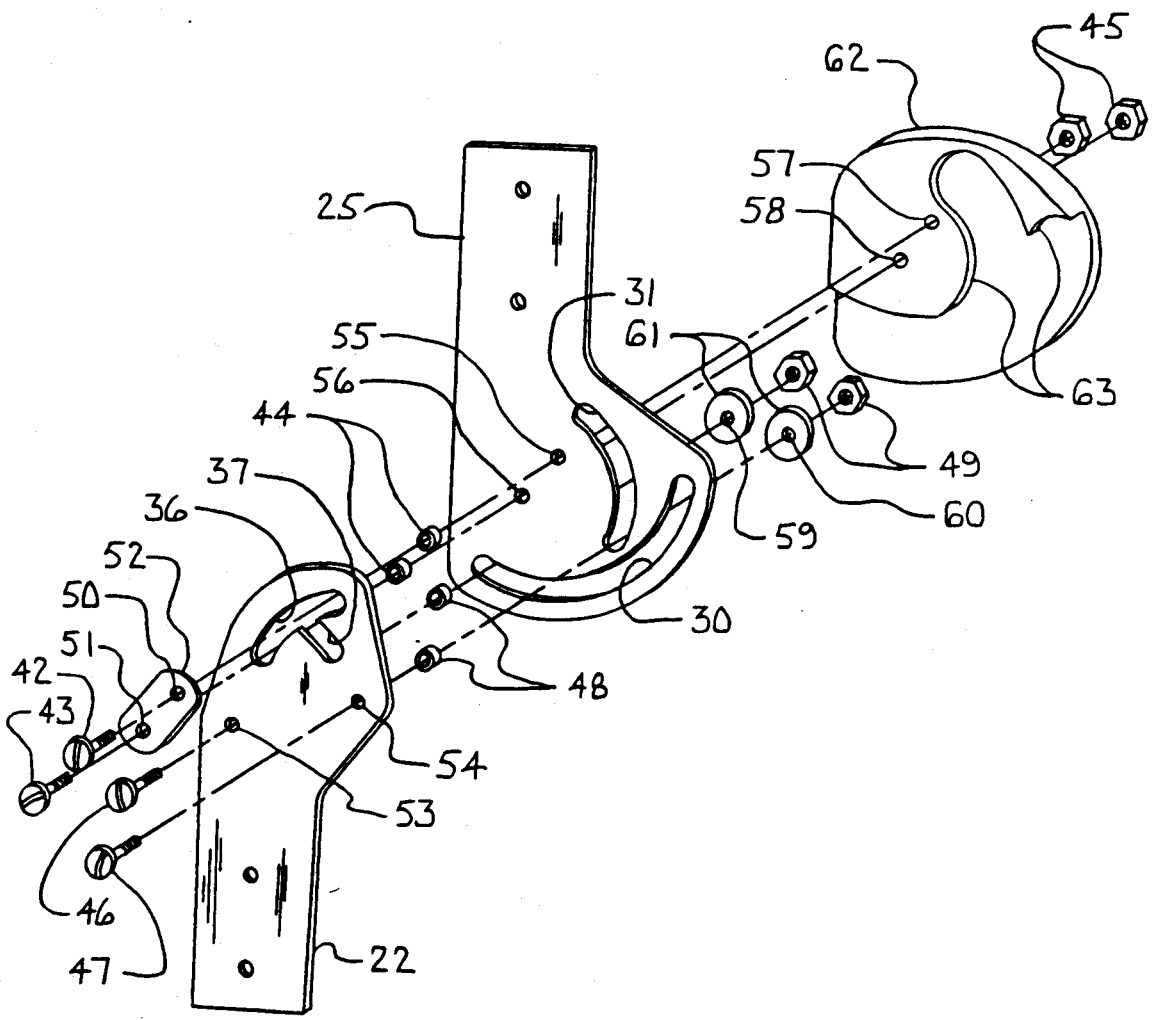
FIG. 14 is an exploded perspective view of a mechanical hinge of the present invention, showing the relative interfitting arrangement of its components.
Figure 15:
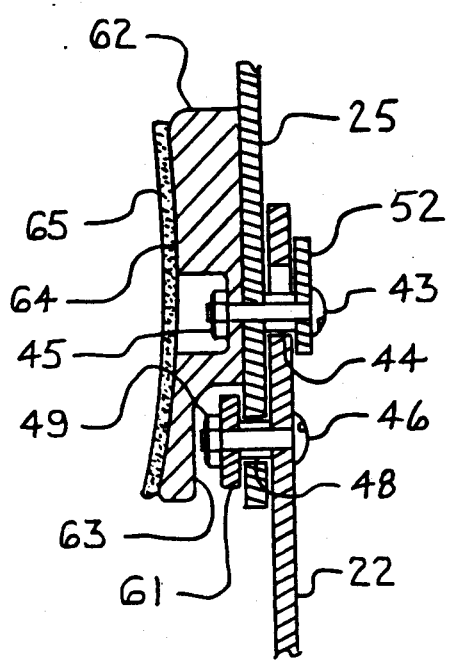
FIG. 15 is a sectional view of the mechanical hinge taken along line 15—15 of FIG. 12.

FIG. 14 depicts an exploded view of the stabilizing mechanical hinge of the present invention. The femoral followers 38 and 39 (see FIG. 12) can be comprised of screws 42 and 43, respectively, as well as nuts 45 and bushings 44. Likewise, the tibial followers 40 and 41 can be comprised of screws 46 and 47, respectively, as well as nuts 49 and bushing 48. Other follower means may be used such as roller bearings or geared rollers used in conjunction with toothed slots, if desired. The screws 42 and 43, respectively, pass through holes 50 and 51 formed in thrust resisting means such as thrust plate 52. Similarly, the screws 46 and 47, respectively, pass through holes 53 and 54 formed in the tibial link 22. Bushings 44 and 48 are provided, having an inside diameter slightly larger than the outside diameter of the screws 42, 43, 46 and 47 which pass through such bushings in bearing relation with respect thereto, and an outside diameter small enough to fit in bearing relation with the slots 37, 36, 30 and 31, respectively. The screws 42 and 43 then pass through holes 55 and 56 formed in the femoral link 25 and also through holes 57 and 58 formed in the condylar pad 62, respectively, and are then fastened by nuts 45. Likewise, the screws 46 and 47, respectively, pass through holes 59 and 60 formed in such thrust resisting means as thrust washers 61, and are then fastened by nuts 49 to complete the mechanical joint. The thrust plate 52 and thrust washers 61 serve as reaction members to prevent the femoral link 25 and tibial link 22 from separating when subjected to a blow on its side or normal to the plate or link. The condylar pads 62 are disposed on the medial and lateral sides of the knee to prevent lateral displacement of the femur with respect to the tibia (see FIGS. 3 and 4). Condylar pads 62 are essentially semi-oval in shape and can be made of plastic such as polyethylene. The flat portion of the condylar pad which mates with the femoral link 25 is formed to have recesses 63 to allow clearance for the thrust washers 61 and nuts 49 (see FIG. 15). A cavity 64 is formed on the interior or leg side surface of the condylar pad 62 to accommodate nuts 45 and the ends of screws 42 and 43 as shown in FIG. 15. The condylar pad may be lined with shock absorbent material 65 (see FIG. 15) such as polyurethane or polyethylene foam for comfort.

Alternatively, if some rotation of the condylar pad 62 is desired to better comform to the knee as the joint is flexed the pad 62 may be attached by one of screws 42 or 43 with a single nut 45 and the other screw terminated with a washer and a nut 45 on the inside of the femoral link 25 similarly to screws 46 and 47 and nuts 49.

Figure 16:
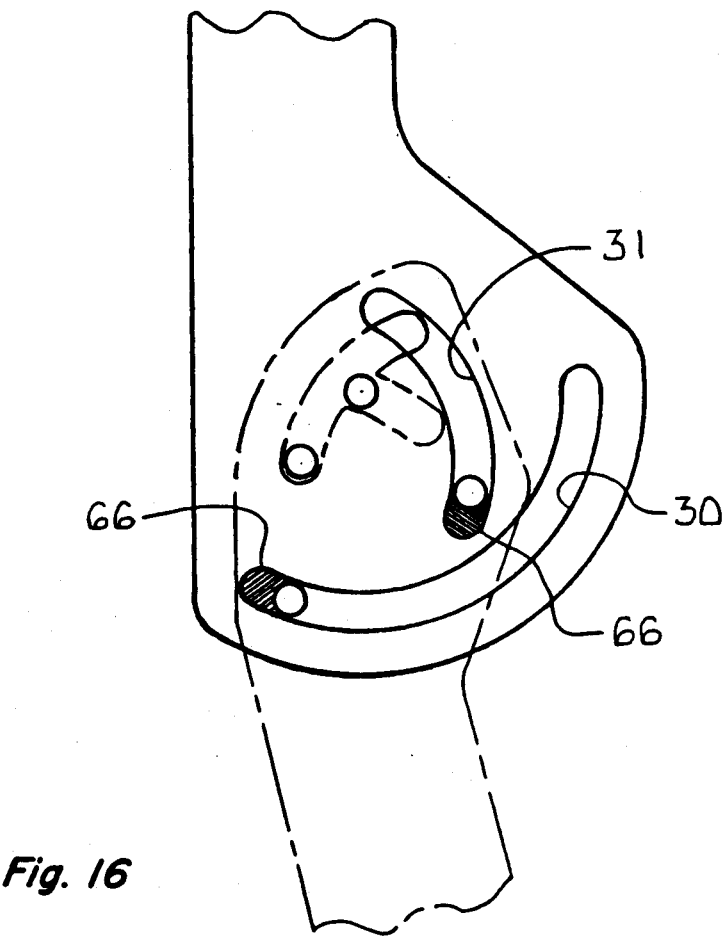

Restriction in flexion and/or extension of the knee joint may be necessary to prevent the user with a knee injury from reinjuring the knee by either flexing or extending it beyond the user's limit. The range of motion to the knee joint may be controlled in several ways. First, the length of one or more of the slots 30, 31 and 36 may be controlled to achieve the desired range of motion. Secondly, the slots 30, 31, 36 and 37 which already have full length for the normal range of motion may be shortened by applying on epoxy or other resin 66 to the ends of one or more slots 30, 31 and 36 to achieve the desired limited range of motion, as shown in FIG. 16. Third, referring to FIG. 17, the terminal end of the femoral link 67 can be enlarged, two slots 68 and 69 incorporated and stop members 9 comprising a screw, a thick washer and nut may be fixed within the slots to limit the range of motion of the tibial link 70.

A protective knee cup may be used in conjunction with the knee brace. The femoral link 71, as shown in FIG. 18, can be modified to provide a mounting for knee cup 72. The slot 73 is formed in femoral link 71 and a strap 74 with Velcro closures or other closure means holds the knee cup 72 onto the femoral link 71.

Another method of mounting a protective knee cup is shown in FIG. 19. The tibial link 75 can be modified to provide mounting for the knee cup 72. The end of a strap 76 is fastened by means 77, i.e. screw and nut to the tibial link 75. The opposite end of the strap 76 with Velcro closures or other closure means holds the knee cup 72 onto the tibial link 75.

Thus there had been shown and described a variable axis brace which meets the objects of the invention. Although the preferred embodiments of the invention have been described, it will be apparent to those skilled in the art that many changes, modifications, variations and applications might be made with respect to the invention, including the choice of materials and the design of the joint elements. All such changes, modifications, variations and applications are intended to be within the scope of this invention which is limited only by the following claims.

I claim:

1. A stabilizing mechanical hinge for use in a knee brace for simulating the functions of the articulating members in the human knee, said brace having leg grasping means for clasping the brace to wearer's leg and means defining a mechanical hinge at the lateral and medial sides of the human knee, said hinge comprising:

a femoral joint element including at least one femoral arcuate slot formed through said femor joint element with center of curvature located at the femoral attachment point of a cruciate ligament;

a tibial joint element including at least one tibial arcuate slot formed through said tibial joint element with center of curvature located at the tibial attachment point of a cruciate ligament;

at least one femoral pivot and bearing means carried by said femoral joint element, said femoral pivot and bearing means located at the center of curvature of said femoral arcuate slot and having a surface in bearing engagement with said tibial arcuate slot, at least one tibial pivot and bearing means carried by said tibial joint element, said tibial pivot and bearing means located at the center of curvature of said tibial arcuate slot and having a surface in bearing engagement with said femoral arcuate slot;

thrust resisting means mounted to said femoral pivot and bearing means and confining said tibial joint element between said femoral joint element and said thrust resisting means; and thrust resisting means mounted to said tibial pivot and bearing means and confining said femoral joint element between said tibial joint element and said thrust resisting means.

2. The stabilizing mechanical hinge according to claim 1 wherein said femoral joint element includes an anterior arcuate slot with center of curvature located at the femoral attachment point of the anterior cruciate ligament and a posterior arcuate slot with center of curvature located at the femoral attachment point of the posterior cruciate ligament formed through said femoral joint element, and the tibial pivot and bearing means includes a pair of said pivot and bearing means, each of said pivot and bearing means having a surface in bearing engagement with said femoral joint element arcuate slots.

3. The stabilizing mechanical hinge according to claim 1 wherein said tibial joint element includes an anterior arcuate slot with center of curvature located at the tibial attachment point of the anterior cruciate ligament and posterior arcuate slot with center of curvature located at the tibial attachment point of the posterior cruciate ligament formed through said tibial joint element and the femoral pivot and bearing means includes a pair of said pivot and bearing means, each said pivot and bearing means having a surface in bearing engagement with said tibial joint element arcuate slots.

4. The stabilizing mechanical hinge according to claim 1 wherein said femoral joint element includes an anterior arcuate slot with center of curvature located at the femoral attachment point of the anterior cruciate ligament and a posterior arcuate slot with center of curvature located at the femoral attachment point of the posterior cruciate ligament and a pair of pivot and bearing means each located at the center of curvature of the respective arcuate slots, and said tibial joint element includes an anterior arcuate slot with center of curvature located at the tibial attachment point of the anterior cruciate ligament and a posterior arcuate slot with center of curvature located at the tibial attachment point of the posterior cruciate ligament and a pair of pivot and bearing means, each located at the center of curvature of said arcuate slots.

5. The stabilizing mechanical hinge according to claim 4 wherein a line through said pair of femoral joint element pivot and bearing means carried by said femoral joint element forms an approximately 40° angle with the long axis of the femur of a wearer's leg.

6. A stabilizing mechanical hinge for use in a knee brace for simulating the functions of the articulating members in the human knee, said brace having leg grasping means defining a mechanical hinge at the lateral and medial sides of the human knee, said hinge comprising:

a femoral joint element including an anterior arcuate slot with center of curvature located at the femoral attachment point of the anterior cruciate ligament and a posterior arcuate slot with center of curvature located at the femoral attachment point of the posterior cruciate ligament formed through said femoral joint element;

a tibial joint element including a pair of pivot and bearing means carried by said tibial joint element, each said pivot and bearing means having a surface in bearing engagement with a respective arcuate slot of said femoral joint element; and thrust resisting means mounted to said tibial joint element pivot and bearing means confining said femoral joint element between said tibial joint element and said thrust resisting means.

7. A stabilizing mechanical hinge for use in a knee brace for simulating the function of the articulating members in the human knee, said brace having leg grasping means for clasping the brace to the wearer's leg and means defining a mechanical hinge at the lateral and medial sides of the human knee, said hinge comprising:

a femoral joint element including a femoral anterior arcuate slot with center of curvature located at the femoral attachment point of the anterior cruciate ligament and femoral posterior arcuate slot with center of curvature located at the femor attachment point of the posterior cruciate ligament formed through said femoral joint element;

a tibial joined element including a combined tibial anterior arcuate slot with center of curvature located at the tibial attachment point of the anterior cruciate ligament and an intersecting tibial posterior arcuate slot with center of curvature located at the tibial attachment point of the posterior cruciate ligament formed through said tibial joint element;

a pair of femoral pivotal and bearing means carried by said femoral joint element, each said femoral pivot and bearing means located at the center of curvature of said respective femoral arcuate slots and each having a circumferential surface in bearing engagement with said respective tibial arcuate slots, wherein a line through said pair of femoral pivot and bearing means forms an approximately 40° angle with the long axis of the femur of the wearer's leg;

a pair of tibial pivot and bearing means carried by said tibial joint element, each said tibial pivot and bearing means located at the center of curvature of said respective tibial arcuate slots and each having a circumferential surface in bearing engagement with said respective femoral arcuate slots;

a thrust plate mounted to said pair of femoral pivot and bearing means and confining said tibial joint element between said femoral joint element and said thrust plate; and a pair of thrust washers each mounted to said respective tibial pivot and bearing means and confining said femoral joint element between said tibial joint element and said pair of thrust washers.

8. In a knee brace for supporting an unstable knee joint through all range of articulation, the combination of:

a femoral brace shaped to fit over the frontal upper leg;

a tibial brace shaped to fit over the frontal lower leg;

said femoral and tibial braces being joined by medial and lateral mechanical hinge joints, each said hinge joint comprising:

a femoral joint element including at least one femoral arcuate slot formed through said femoral joint element with center of curvature located at the femoral attachment point of a cruciate ligament, a tibial joint element including at least one tibial arcuate slot formed through said tibial joint element with center of curvature located at the tibial attachment point of a cruciate ligament, at least one femoral pivot and bearing means carried by said femoral joint element, said femoral pivot and bearing means located at the center of curvature of said femoral arcuate slot and having a surface in bearing engagement with said tibial arcuate slot, at least one tibial pivot and bearing means carried by said tibial joint element, said tibial pivot and bearing means located at the center of curvature of said tibial arcuate slot and having the bearing surface in bearing engagement with said femoral arcuate slot, thrust resisting means mounted to said femoral pivot and bearing means and confining said tibial joint element between said femoral joint element and said thrust resisting means, and thrust resisting means mounted to said tibial pivot and bearing means and confining said femoral joint element between said tibial joint element and said thrust resisting means;

said femoral brace being formed with an enlarged paddle to prevent said femoral brace from sinking into the soft tissue of said upper leg;

said tibial brace being formed with an enlarged paddle to prevent said tibial brace from sinking into the soft tissue of said lower leg; and means for attaching said femoral and tibial braces to a leg.

9. The knee brace according to claim 8 wherein a lower portion of said femoral brace and an upper portion of said femoral brace partially encircles the upper leg, and wherein the lower frontal edge of the said femoral brace is formed as an elongated semicircle to minimize pressure on the quadriceps muscles.

10. The knee brace according to claim 8 wherein an upper portion of said tibial brace and a lower portion of said tibial brace partially encircles the lower leg, and said upper portion of said tibial brace conforms to the tibia tubercle to minimize the displacement of the tibia with respect to the femur.

11. The knee brace as described in claim 10 wherein said upper portion of said tibial brace is formed with a concave notch to minimize pressure on the patella tendon and the lower part of the patella.

12. The knee brace according to claim 8 wherein integral slots are formed in each of the respective ends of said lower and upper portions of said femoral and tibial braces, and including:

a pair of wide straps through said slots in said femoral brace and a pair of wide straps through said slots in said tibial brace forming said means for leg attachment.

13. The knee brace according to claim 8 further including:

a pair condylar pads wherein each said condylar pad is attached to respective femoral joint elements of said mechanical hinge joints, and whereby said condylar pads engage the respective medial and lateral sides of the knee joint to prevent lateral displacement of the femur with respect to the tibia of said knee joint.

* * * * *

UNITED STATES PATENT AND TRADEMARK OFFICE
CERTIFICATE OF CORRECTION

PATENT NO. : 5,009,223

DATED : April 23, 1991

INVENTOR(S) : Michael A. DeFonce

It is certified that error appears in the above—identified patent and that said Letters Patent is hereby corrected as shown below:

Column 6, line 51, "femor" should be --femoral--;

Column 8, line 18, "femor" should be --femoral--;and

Column 8, line 28, "pivotal" should be --pivot--

Signed and Sealed this

Twenty-ninth Day of September, 1992

Attest:

DOUGLAS B. COMER

*Attesting Officer*  *Acting Commissioner of Patents and Trademarks*